(12) United States Patent
Lang et al.

(10) Patent No.: US 9,010,331 B2
(45) Date of Patent: Apr. 21, 2015

(54) PATIENT INTERFACE STRUCTURE AND METHOD/TOOL FOR MANUFACTURING SAME

(75) Inventors: Bernd Christoph Lang, Graefelfing (DE); Achim Biener, Aufkirchen (DE); Johannes Nickol, München (DE)

(73) Assignee: ResMed Limited, Bella Vista (AU)

( * ) Notice: Subject to any disclaimer, the term of this patent is extended or adjusted under 35 U.S.C. 154(b) by 478 days.

(21) Appl. No.: 12/735,728

(22) PCT Filed: Feb. 12, 2009

(86) PCT No.: PCT/EP2009/000985
§ 371 (c)(1),
(2), (4) Date: Aug. 12, 2010

(87) PCT Pub. No.: WO2009/100905
PCT Pub. Date: Aug. 20, 2009

(65) Prior Publication Data
US 2010/0307504 A1   Dec. 9, 2010

(30) Foreign Application Priority Data
Feb. 13, 2008 (EP) .................................... 08151350

(51) Int. Cl.
*A61M 16/06* (2006.01)
*B29C 45/14* (2006.01)
*A62B 18/02* (2006.01)

(52) U.S. Cl.
CPC .......... *A61M 16/06* (2013.01); *A61M 16/0683* (2013.01); *A61M 16/0616* (2013.01); *A61M 16/0622* (2013.01); *A61M 16/0633* (2013.01)

(58) Field of Classification Search
None
See application file for complete search history.

(56) References Cited

U.S. PATENT DOCUMENTS

2002/0020416 A1   2/2002   Namey
2005/0199239 A1   9/2005   Lang et al.

FOREIGN PATENT DOCUMENTS

DE   10 2005 03365   1/2007
WO   WO 2007/145534   12/2007

OTHER PUBLICATIONS

International Search Report for PCT/EP2009/000985, mailed May 12, 2009.

*Primary Examiner* — Tan-Uyen (Jackie) T Ho
*Assistant Examiner* — Mark Wardas
(74) *Attorney, Agent, or Firm* — Nixon & Vanderhye P.C.

(57) ABSTRACT

Component of a patient interface (1), particularly a cushion, comprising a first portion (3) having a first shore hardness and a second portion (5) having a second shore hardness different from the first shore hardness, wherein the first and second portion are co-molded to each other.

41 Claims, 8 Drawing Sheets

PATIENT INTERFACE STRUCTURE AND METHOD/TOOL FOR MANUFACTURING SAME

This application is the U.S. national phase of International Application No. PCT/EP2009/000985, filed 12 Feb. 2009, which designated the U.S. and claims priority to EP Application No. 08151350.9, filed 13 Feb. 2008, the entire contents of each of which are hereby incorporated by reference.

FIELD OF THE INVENTION

The invention relates to patient interfaces such as breathing masks covering nose and/or mouth of a patient and components or structures thereof as well as to methods for manufacturing such patient interfaces or components thereof and further relates to tools for manufacturing the same. Furthermore, the present invention relates to cushions and pads, such as mask cushions or forehead pads for a patient interface such as a breathing mask. Moreover, the present invention relates to a patient interface or component of a patient interface obtainable by a method according to the present invention as well as to a tool for producing such interface or component and/or for performing a respective method.

The invention concerns, in particular, a pad or cushion and a patient interface such as a breathing mask which is equipped with such pad or cushion. An internal space of a breathing mask is established by the patient interface in conjunction with sealing contact of the pad or cushion with the surface of the face of a user. This internal space is sealed in relation to the ambient atmosphere in such a way that a pressure which is increased in relation to the ambient pressure can be obtained, at least in phase-wise fashion, in the internal space of the patient interface or breathing mask. Breathing masks of that kind are used in particular in connection with the medical or therapeutic administration of breathable gases and also in the technical sector, for example in the sector of breathing apparatus technology. The invention further concerns a sealing and/or contact structure and a process and tool for the production thereof in general.

Usually, with such patient interfaces, the sealing action in relation to the surface of the face of the user of the interface is achieved by a sealing lip structure. Such sealing lip structure, e.g., extends in inwardly directed relationship around an opening of the mask, and is made from an elastically deformable material.

The sealing action achieved with sealing lips of that kind generally increases with the pressure with which the sealing lip is pressed against the surface of the face. In the case of comparatively high contact pressures, in particular long-term use of breathing masks of that kind can give rise to troubles.

BACKGROUND OF THE INVENTION

Patient interfaces and patient interface structures or components, e.g., sealing lips, are known in the prior art, for example, in the field of face masks for delivering breathable air to a patient. In such face masks, often hollow cushions or bent, resilient lip-structures are used for providing contact zones for contacting the face of the user in order to avoid dents and to improve wearing comfort of the user. Furthermore, such structures are used as a sealing structure for sealing the mask interior from the exterior in the contact region where the mask rests on a user's face.

A disadvantage of structures known in the art is that they are complicated to manufacture and a number of manual manufacturing steps is often necessary.

In particular, it is known to fill a hollow mask cushion with silicone or gel wherein the hollow structure is closed by use of a silicone adhesive. Moreover, it is known to separately manufacture different parts of such patient interface components in different steps and to attach them afterwards by mechanical fastening means or structures.

The solutions known in the prior art are in particular, not easy to handle, not durable, complicated and expensive to manufacture, not suitable for automating, not bio-compatible as well as optically and hygienically objectionable. The known solutions are further disadvantageous in that they do not or insufficiently allow individualization and are less comfortable for a wearer.

OBJECT UNDERLYING THE INVENTION

It is an object underlying the present invention to provide a patient interface or a component of a patient interface, such as a cushion or pad, a method for manufacturing, such patient interface and/or component as well as a tool for manufacturing the same which overcome the deficiencies of the prior art. Alternatively or additionally, it is an object underlying, the present invention to provide a patient interface or component thereof which has an improved sealing effect and/or an improved level of wearing comfort. Alternatively or additionally, it is an object underlying the present invention to provide a method for manufacturing a patient interface or component thereof and/or a tool for manufacturing the same which allows efficient and effective production of improved patient interfaces and/or components thereof.

These objects are fulfilled with the features of the claims wherein dependent claims relate to preferred features of the present invention.

SUMMARY OF THE INVENTION

The present invention relates to a patient interface structure or component, e.g., a breathing mask and components thereof. Such components are, e.g., a pad or a cushion for supporting or sealingly supporting a breathing mask or patient interface on a user's skin. Moreover, the present invention relates to a method and tool for manufacturing a patient interface or patient interface component, particularly those according to the present invention.

According to the present invention, a component of a patient interface, such as a face mask, and in particular a patient interface cushion comprises a first portion and a second portion. Preferably, the first portion has a first shore hardness whereas the second portion has a second shore hardness, wherein the second shore hardness differs from the first shore hardness and wherein the first and second portion are co-molded to each other.

Additionally or alternatively, the present invention relates to a component of a patient interface, such as a breathing mask, and in particular to a patient interface cushion comprising a first portion having a first shore hardness and a second portion having a second shore hardness, wherein the first hardness differs from the second shore hardness and wherein the first and second portion are formed integrally with one another.

Preferably, co-molding of the first portion and the second portion results in the first and second portion being formed integrally with one another.

According to a further alternative or additional aspect, the present invention relates to a component of a patient interface, such as a breathing mask, and in particular to a patient interface cushion comprising a first portion having a first material characteristic and a second portion having a second material characteristic wherein such first characteristic of said first portion differs from said second characteristic, and wherein the first and second portion are formed integrally with one another and/or wherein the first and second portion are co-molded to each other.

According to a preferred aspect of the present invention, the first portion and the second portion integrally merge at a merging surface constituting the contact area between said two portions. Said merging surface preferably is a substantially plane surface and/or a surface having a substantially plane cross-section. Preferably, the merging or contact surface does not have undercuts. Also preferably, the first portion and second portion solely merge via such merging surface and/or are not connected by means of structural or mechanical fastening means.

Preferably, when seen in a cross-sectional plane, the contact area between the first and second portions, here the cross-sectional view of the merging surface, is inclined by an angle lying in the range from/between about 0° to/and 20°, preferably from/between about 1° to/and 12° degree and also preferably from/between about 2° to/and 6° and preferably of about 2.5°. Preferably, such angle extends in relation to a longitudinal axis which extends substantially orthogonally with regard to a plane in which the patient interface component contacts a wearer. Additionally or alternatively, said angle extend with regard to an axis along which the component is ejected from a mold.

According to a preferred embodiment, the component of a patient interface according to the present invention is a breathing mask cushion for sealingly supporting a breathing mask on a wearer's face, a forehead pad for supporting a breathing mask on a wearer's face, part of a headband for securing a device such as a breathing mask to a wearer's head or other parts or components for contacting a wearer's body.

Preferably, such cushion comprises a first portion comprising a thin membrane and/or a second portion forming an undercushion being thicker than the first portion and/or the membrane of the first portion.

Preferably, the first portion and the membrane of the first portion, respectively, form an outer portion of the patient interface cushion for, preferably sealingly, contacting a wearer's skin wherein the second portion or undercushion is shielded vis-à-vis the wearer's skin by the first portion. Thus, the second portion preferably does not directly contact the wearer's skin Preferably, the first portion of a patient interface component, here e.g. a mask cushion, comprises a membrane or sealing lip portion and a connection portion. The second portion of the mask cushion correspondingly comprises a cushion portion and a connection portion. The connecting portion of the first portion and second portion of the breathing mask cushion, respectively, form a merging surface or contact area along which the first and second portion merge. Preferably, the second portion is co-molded to the first portion along the contact area or merging surface.

The cushion portion of the second portion forms an undercushion of the breathing mask cushion which is shielded or covered vis-à-vis a wearer by a membrane or sealing lip portion of the first portion which at least partially extends along and over the second portion and the undercushion portion, respectively.

The second portion is located in the mask interior whereas the first portion of the mask cushion is located at the outside of the mask facing towards the outside environment or a wearer, respectively.

Preferably, the first and second portion are made of or comprise the same material or two materials of the same group of materials, preferably silicone, wherein the first portion has a first material characteristic and the second portion has a second material characteristic different from the first material characteristic. Preferably, said characteristic is shore hardness. Preferably, the (first) shore hardness of the first portion is higher than the (second) shore hardness of the second portion. Preferably, the second shore hardness lies in a range between about 1 and 40, preferably between about 3 and 25 and more preferably between 5 and 10 shore A. The first shore hardness preferably lies in the range between about 10 and 100, more preferably between about 20 and 60 and even more preferably between about 35 and 45 shore A.

The hardness of the materials is, in accordance with a preferred embodiment of the present invention, measured in shore A according to preferably according to DIN 53505.

Preferred materials are resilient or elastic materials allowing application of different hardnesses. According to a preferred embodiment, the first and/or second portion comprises a polymer, e.g., a polysiloxane; silicone; liquid silicone rubber, foamed materials, foamed silicone and/or thermoplastic elastomer.

The breathing mask cushion and patient interface, respectively, preferably comprises a longitudinal axis extending generally perpendicular to a contact plane in which the cushion or interface substantially contacts a wearer. Preferably, the contact region or merging surface between the first portion and the second portion is inclined with regard to said axis. Preferably, the contact region or merging surface surrounds said axis and is inclined in a frusto-conical way, opening in direction away from the wearer.

In addition or alternatively, the present invention relates to a method for producing a component of a patient interface or a patient interface, respectively. In particular, the method according to the present invention relates to the production of a patient interface or component of a patient interface, such as a breathing mask cushion, as discussed and disclosed in the present application. A preferred method according to the present invention comprises the steps of providing a molding tool having a first mold part and a second mold part which are adapted to define a first mold cavity therebetween for molding a first portion of said patient interface or patient interface component. A first material having first material characteristics such as a first shore hardness is injected into the first molding tool and into the first cavity defined thereby in order to provide the first portion of the component. After said first material has been injected into the first cavity and has at least partially solidified or fully solidified the first mold cavity is opened by removing the second mold part from the first mold part wherein the first portion which has been injection molded so far remains inside the first mold part. Next, a third mold part is provided so that a second mold cavity is established between the first mold part and/or the first portion which has been previously injection molded and the third mold part.

A second material having a second material characteristic, such as a second shore hardness, is then injected into the second mold cavity in order to provide a second portion integral with the first portion.

Preferably, as discussed above with regard to the patient interface or patient interface component according to the present invention, the first material characteristic and the second material characteristic, such as the first shore hardness and the second shore hardness, differ from one another wherein, preferably, a first shore hardness is larger than the second shore hardness.

Preferably, the first mold part constitutes a first mold half wherein the second mold part and the third mold part, respectively, constitute a second mold half. The second mold part and the third mold part are preferably arranged around a turntable on which the first mold part is provided. After the first portion has been injection molded the second mold half is removed from the first mold half and the first mold part is provided by turning of the first mold half on a turntable and by placing it in a defined position in relation to the third mold half thereby so that a second cavity is defined. Then, the second part is injection molded.

Preferably, the first mold half comprises a third cavity forming part of or an extension of the first cavity for molding a part of the first portion when the first material is injected into the first cavity. Accordingly, the third cavity forms part of the first cavity and is filled in a first injection shot with the first material as is the first cavity. The third cavity is preferably defined in the first mold part. According to a preferred aspect, the first mold part comprises two parts which define the third cavity between them. The third cavity is preferably defined such that the first portion can be easily withdrawn from the tool without the need to significantly open the third cavity and/or without the need to place the two parts of the first mold part substantially distanced to one another.

When the second mold part is replaced by the third mold part the third cavity remains and the second cavity is formed. However, since the third cavity had been filled with the first material already in the first injection shot it does not form part of the second cavity.

After the second injection shot with which the second material of the second portion has been injected into the second cavity is finalized the tool is opened and the patient interface component can be ejected or withdrawn from the tool.

The method according to the present invention may also be carried out in that the order of the single method steps is changed. For example, the second portion may be molded firstly wherein the first portion is molded after the second one. The tool will then be adapted accordingly.

Moreover, the present invention is not limited to injection molding. Other manufacturing methods, such as molding of foamed materials may be applied and are well within the scope of the present invention.

According to a further aspect of the present invention, there is provided a tool for manufacturing a patient interface or a patient interface component as discussed in the present application and/or for performing a method as discussed in the present application. Aspects of such tool have already been discussed in combination with the patient interface component or the method of the invention.

Such tool comprises a first mold part and a second mold part which are adapted to define a first mold cavity therebetween. There is further provided a third mold part adapted to define a second mold cavity between the first mold part and/or an injected first portion of a patient interface component and the third mold part. Preferably, the first mold part provides a third cavity forming a part or an extension of the first cavity.

Preferably, the second mold part defines an inner wall of the said first cavity whereas a third mold part defines an inner wall of said second cavity. The outer wall of said second cavity is preferably formed by or comprises the merging surface or contact surface formed by the first portion of the patient interface component.

The outer walls of the third cavity are preferably formed by respective surfaces of the first mold part alone. However, said first mold part may comprise two separable components of which a first one defines the outer wall of the third cavity and preferably the outer wall of the first cavity and wherein the second part forms an inner wall of the third cavity and an outer wall of the second cavity.

The present invention is of particular advantage in that it provides an improved patient interface and patient interface component such as a breathing mask cushion with enhanced characteristics. In particular, the patient interface and patient interface component according to the present invention allows improved comfort for a wearer and avoids reddening and pressure marks occurring on a wearer's face. Moreover, the present invention allows the provision of special geometries of a patient interface and a patient interface component for improved compliance with a user's physiognomy and anthropometry. The present invention particularly allows efficient and effective production of improved patient interfaces and/or components ant an automatised production. Moreover, optically and hygienically as well as structurally improved patient interfaces and patient interface components can be provided. In particular, individualization and comfortable wearing of such improved patient interfaces and patient interface components is allowed by the two component technology discussed and disclosed in this application.

For example the use of a first and second material allows the provision of a soft and comfortable material for e.g. comfortably supporting a patient interface on a users skin and of a harder material for providing improved haptic and hygienic properties and for allowing the provision of, additional fastening means for, e.g., securing a patient interface component to a patient interface frame.

The method and tool according to the present invention particularly provide for a effective and efficient manufacturing of an improved patient interface or patient interface component having a improved characteristics. Also, the hardness and geometry of the patient interface or patient interface component may be easily adjusted or individualized without the need of an exchange of expensive tool components. Rather, e.g., a second and/or third mold part may be easily replaced or exchanged in order to adjust the above-listed characteristics wherein the first mold part can be maintained. Moreover, the production of an improved patient interface or patient interface component with improved properties as regards comfort etc. is achieved in an easy and cheap manner in an automized process. Also, the present invention allows an improved production of harmonized and exchangeable modules for patient interfaces wherein the interface measures are maintained while only features relevant for the individual improvement of the patient interface or patient interface component are adjusted.

The present invention particularly allows to manufacture one silicone part molded with two hardness zones for use as, e.g., forehead pads (higher hardness for the attachment mechanism to the mask and lower hardness towards the patient) or an enhanced cushion to be attached to standard or harmonized frame interfaces.

The present invention furthermore allows to optimize the structure of a patient interface and patient interface component, respectively, based on e.g. different material characteristics. Thus, e.g., the less sticky surface of silicone of a high hardness can be used for providing a thin membrane (sealing lip membrane) for contacting a wearer's skin in combination with a portion of low hardness for supporting the mask, hidden behind the thin harder membrane. This is also combinable with hard contact or fastening or support area(s) towards a mask frame for attachment of the component to the mask. At the same time, the production of such patient interface component is achieved in an effective and efficient manner.

According to preferred embodiments, the present invention allows to co-mold a low hardness undercushion to a high hardness overcushion, preferably in one tool. There is provided, e.g., a low hardness (e.g. 5-10 Shore A) separately molded silicone undercushion. and a high hardness, preferably thin, overcushion. Preferably, one of the two portions, such as the low hardness under cushion comprises colour particles so that is has a predefined visual appearance. Preferably, the present invention allows to manufacture such multi characteristic patient interface or patient interface component in one part and in one tool. At the same time it allows to be fitted to existing, non-modified frames.

Preferably, the tool according to the present invention is built as a tool on a turn table machine. The present invention allows to adjust the hardness/geometry of the low hardness undercushion by changing only one insert in the tool. It thus allows for anthropometrical adjustments in the tool with limited effort and/or costs.

In accordance with an aspect of the present invention there is provided a patient interface component for a breathing mask comprising a receiving opening which in the position of application of the breathing mask coincides at least with the nose and/or mouth opening region of a user of the mask, and a sealing lip which is formed from an elastomer material and which extends around the receiving opening and which in the application position fits on the surface of the face of the user of the mask. Said patient interface component may comprise zones of thickened cross-section.

In that way it is advantageously possible to provide a mask pad device which is distinguished by particularly high adaptability to the most widely varying individual face structures.

The patient interface according to the invention can be of such a nature that it can be fitted for example by way of a peripheral edge portion in sealing relationship to a dish-shaped or arch-shaped body in the form of a hard shell member. That makes it possible for the mask pad device to be removed from the hard shell member for cleaning or replacement purposes.

As an alternative to the measure described hereinbefore it is also possible for the patient interface component to be formed integrally with the dish-shaped or arch-shaped body. That avoids the formation of a gap region between the patient interface or interface component and the dish-shaped or arch-shaped body.

The patient interface can be so designed that the radial cross-sections, that is to say the cross-sections of the mask pad device, vary.

The above-described patient interface component forms a component part of a patient interface such as a breathing mask which, in the application position, engages over the nose and/or the mouth region of the user of a mask. It can be used in a corresponding configuration in relation to a nasal mask and also in relation to a mouth or full-face mask.

The configuration according to the invention of the cross-section of the elastomer structures can also be used in relation to a forehead contact element. Thus, in accordance with a further and also alternative concept, it is possible for forehead contact pads to be of such a configuration that the deformation characteristics thereof are imparted by elastomer components of reduced Shore hardness and/or by zones of increased pore volume.

Although the present application discusses the provision/production of a first portion and a second portion it is apparent for the person skilled in the art that also third and further portions having individual characteristics may be provided/produced.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings:

FIG. 7 are schematic three dimensional views of a patient interface component according to an embodiment of the present invention, wherein

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, each single feature or combination of features in any of the embodiments may constitute an additional embodiment.

In this specification, the word "comprising" is to be understood in its "open" sense, that is, in the sense of "including", and thus not limited to its "closed" sense, that is the sense of "consisting of". A corresponding meaning is to be attributed to the corresponding words "comprise", "comprised" and "comprises" where they appear.

Figure 1:
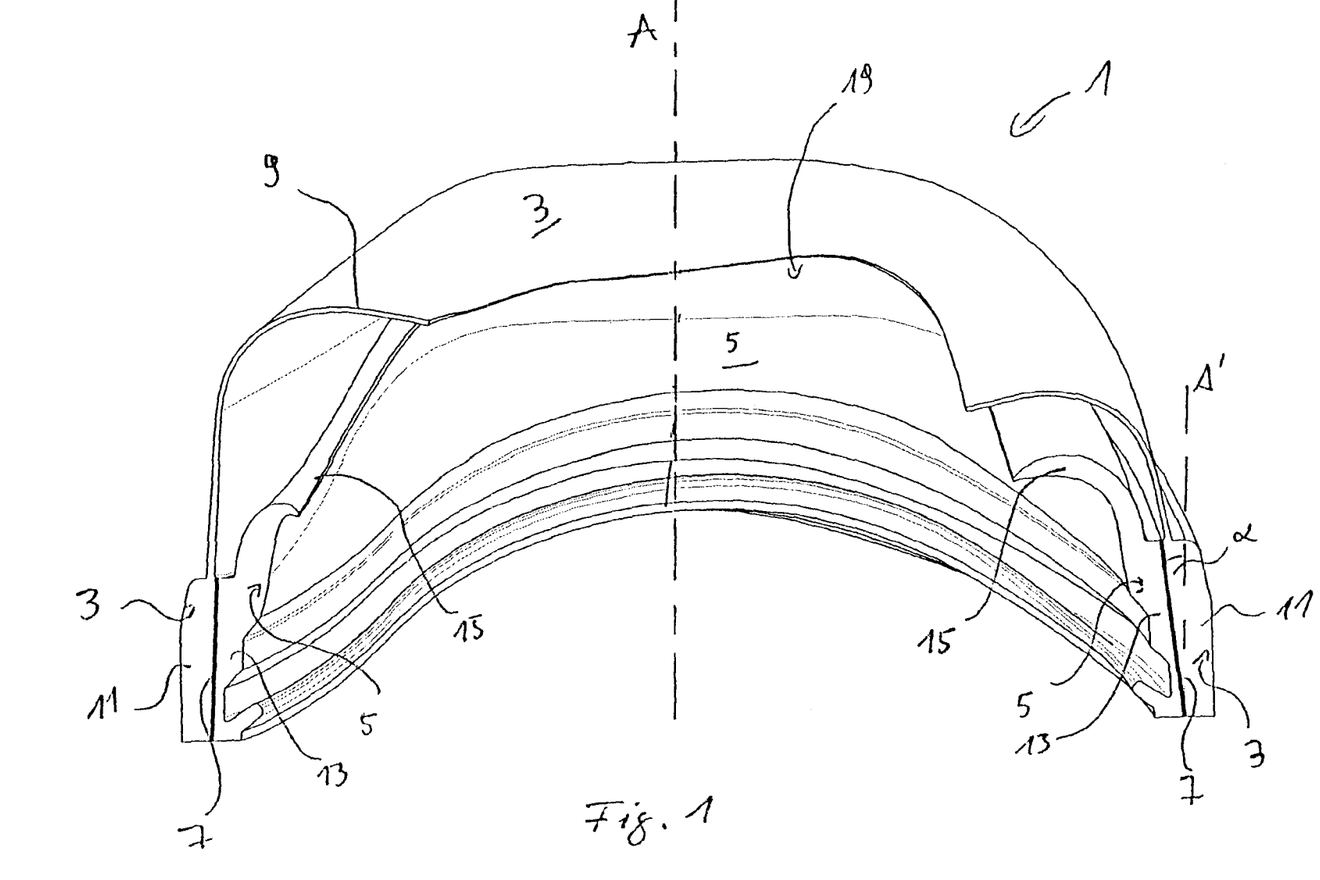
FIG. 1 is a schematic three dimensional cross-sectional view of a patient interface component according to an embodiment of the present invention.

In accordance with the present invention, FIG. 1 shows a patient interface component 1, here a mask cushion for sealingly supporting a breathing mask body on a wearer's face in order to sealingly cover mouth and/or nose of a wearer or patient. Such breathing masks and breathing mask components are used in the treatment of sleep disordered breathing with e.g. breathing means such as CPAP or BiPAP devices wherein a breathing hose for conducting breathing gas is connected to a patient interface such as a breathing mask in order to supply breathing gas to a patient from, e.g., a blower unit.

The patient interface component or cushion 1 shown in FIG. 1 comprises a first portion 3 and a second portion 5. As discussed above, the first portion 3 has a first characteristic such as a first shore hardness whereas the second portion 5 has a second characteristic such as a second shore hardness. Preferably, the first hardness differs from the second hardness. More preferably, the hardness of the first portion 3 is higher than that of the second portion 5.

As discussed above, the first and second portion are formed integrally with one another and are preferably co-molded to each other. As can be seen in FIG. 1 the first portion and the second portion integrally merge at a merging surface or contact surface 7.

As can be seen in FIG. 1, merging surface or contact surface 7 is a preferably substantially plane surface and/or has a plane and/or straight surface cross section, preferably without undercuts. As can be seen in FIG. 1 a patient interface component 1 has a closed profile substantially extending around a longitudinal axis A. Such profile may have a substantially round, triangular, rectangular or polygonal shape. Merging or contact surface 7 preferably extends along said profile and around longitudinal axis A.

The surface 7 is preferably inclined with regard to axis A by an angle α wherein the value of said angle α is preferably in the range as discussed above and is most preferably about 2.5°. Angle α is schematically indicated in FIG. 1 with relation to an axis A' which is parallel to axis A. Axis A is preferably substantially parallel to the walls of a cylinder enveloping said patient interface component 1.

Preferably, the first component 3 comprises a thin membrane or thin sealing lip 9 for sealingly contacting a wearer's skin and a connection portion 11 for connecting said first portion 3 to said second portion 5 and/or fluffier components of a patient interface such as a mask frame (not shown). The second portion 5 of the patient interface component 1 correspondingly comprises a connection portion 13 for connecting said second portion 5 to the first portion 3 and/or further components of a patient interface such as a mask frame (not shown) as well as a cushion portion 15 for comfortably supporting the patient interface component 1 on a wearer's face.

Figure 2:
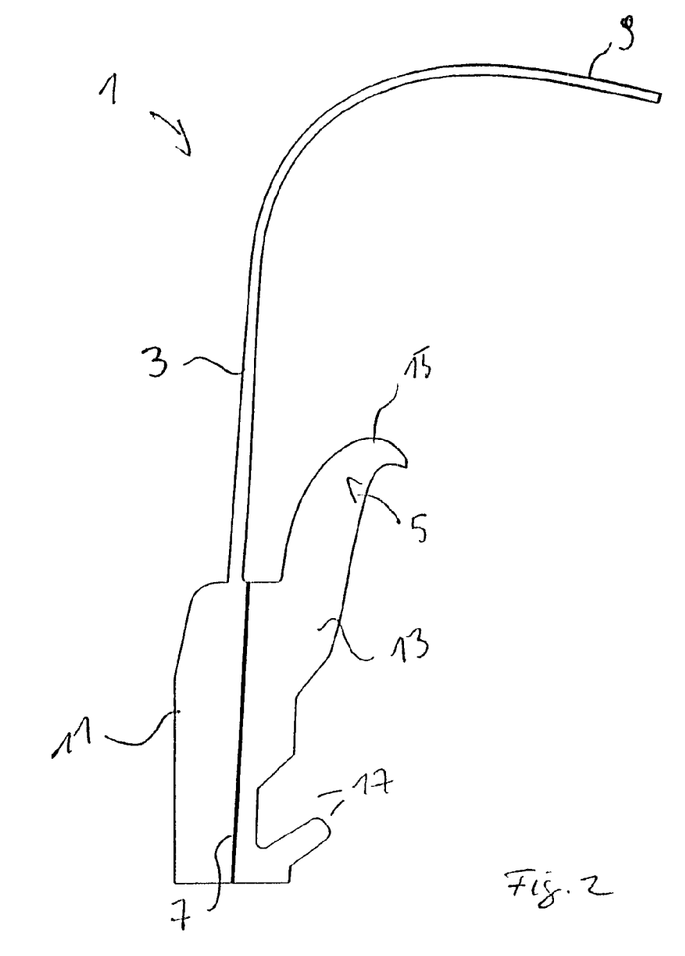
FIG. 2 is a schematic cross-sectional view of a portion of a patient interface component according to an embodiment of the present invention.
Figure 3:
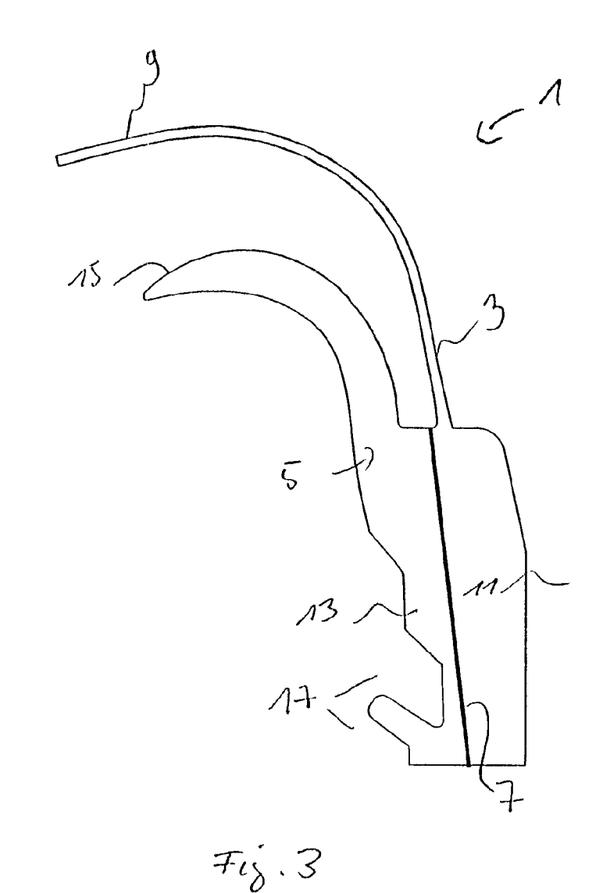
FIG. 3 is a schematic cross-sectional view of a portion of a patient interface component according to an embodiment of the present invention.

FIGS. 2 and 3 show cross-sectional views of preferred embodiments of patient interface component 1 wherein the basic structure corresponds to the embodiment shown in FIG. 1. Alternatively or additionally, FIGS. 2 and 3 show cross sections through the embodiment according to FIG. 1 wherein the person skilled in the art will appreciate that the geometric configuration of the patient interface component and particularly the first portion 3 and the second portion 3 may vary along the circumference of the patient interface component 1 (see FIG. 7). Accordingly, thickness, length, height, etc. of the various portions and components may be adapted to optimally apply to the patient's needs such as patient's physiognomy.

As discussed, in the patient interface component of the present invention such as the patient interface component 1 shown in FIGS. 1-8, the first portion 3 is preferably made of a first material having a high hardness whereas the second portion 5 is made of a second material having a lower hardness. Preferably, both first portion 1 and second portion 5 are made from e.g. liquid silicone rubber or silicone foam wherein the less hard second portion 5 may have a more sticky surface than the harder first portion 3. The surface of the sealing lip portion 9 of first portion 3 preferably has enhanced surface properties and haptic characteristics of the harder material whereas its higher hardness is compensated by a thin geometry in the region of the sealing lip portion 9 for comfortably contacting a user's skin. Since said hard but thin sealing lip membrane 9 is, due to its geometric extensions, preferably too soft for providing resilient support of the mask on its own the second portion 5 being located (from a patient's perspective) underneath said first portion 3 is provided with a thick cushion portion 15. Said cushion portion is preferably thick enough to provide a reliable support of the patient interface component 1 on a wearer's skin. It simultaneously provides optimized resilient characteristics for achieving a comfortable seat and support of a patient interface component such as a mask cushion on a wearer's face due to its low hardness. Potentially sticky or non-optimal surface properties or haptics of such soft second component 5 are compensated by the provision of membrane 9 of a material having differing characteristics. It is appreciated that the geometry and the extensions etc. of the first portion 3 and the second portion 5 as well as the membrane 9 and cushion portion 15 may change or vary along the extension of the patient interface component 1 depending on, e.g., the patient's physiognomy and/or the forces necessary for supporting and/or sealing on a wearer's face.

First portion 3 and second portion 5 each comprise a connection portion 11, 13 which merge at the merging surface or contact surface 7.

Depending on the desired or individual needs, connection portion 11 and/or connection portion 13 are provided with fastening and/or sealing means (for example shown at 17 in FIGS. 2 and 3) for connecting and/or sealing the patient interface component 1 to further structures of a patient interface such as a mask frame (not shown). The geometry of such sealing and/or fastening means preferably depends on the material and/or geometry of the mask frame and the connection portion 11; 13. According to a preferred embodiment, connection portion 11 of the first portion 3 being of a harder material exhibits fastening means whereas connection portion 13 of the less hard second portion 5 exhibits sealing means so that the patient interface component 1 can be sealingly secured to, e.g., a mask frame.

Figure 4:
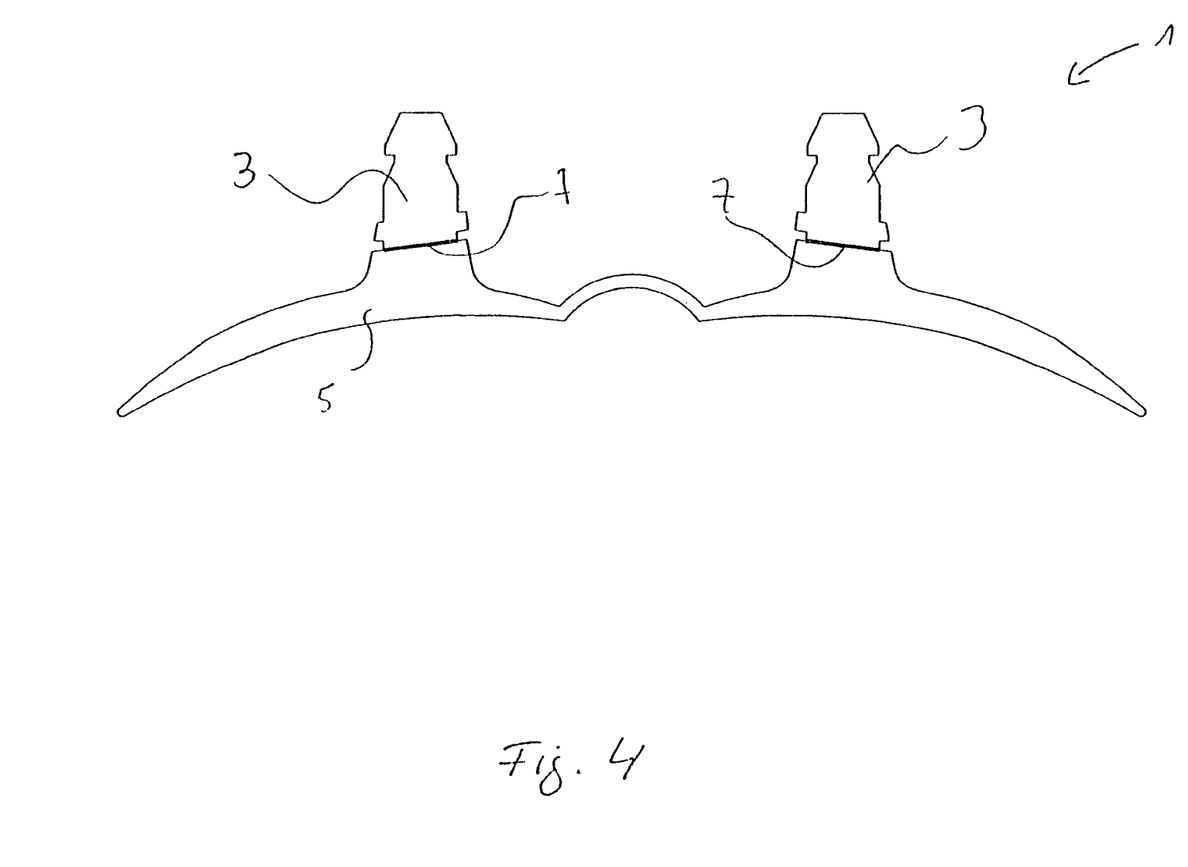
FIG. 4 is a schematic cross-sectional view of a portion of a patient interface component according to an embodiment of the present invention.

FIG. 4 shows a preferred embodiment of a patient interface component 1 according to the present invention, here a forehead support comprising a first portion 3 and a second portion 5 merging at a merging surface or contact surface 7 wherein the first portion 3 is made of a first material having a first hardness whereas the second portion 5 is made of a second material having a second hardness wherein the second hardness is lower than the first hardness. Accordingly, the second material and the second hardness of the second portion 5 of the embodiment shown in FIG. 4 is particularly suitable for supporting the forehead support on a wearer's skin whereas the harder material of the first component 3 is particularly suitable for connecting the patient interface components 1, here a forehead support, to a patient interface such as a face mask or a face mask frame (not shown). As regards further features of the embodiment shown in FIG. 4 it is referred to the above discussion, particularly with regard to FIGS. 1 to 3 and 5 to 8.

Figure 5:
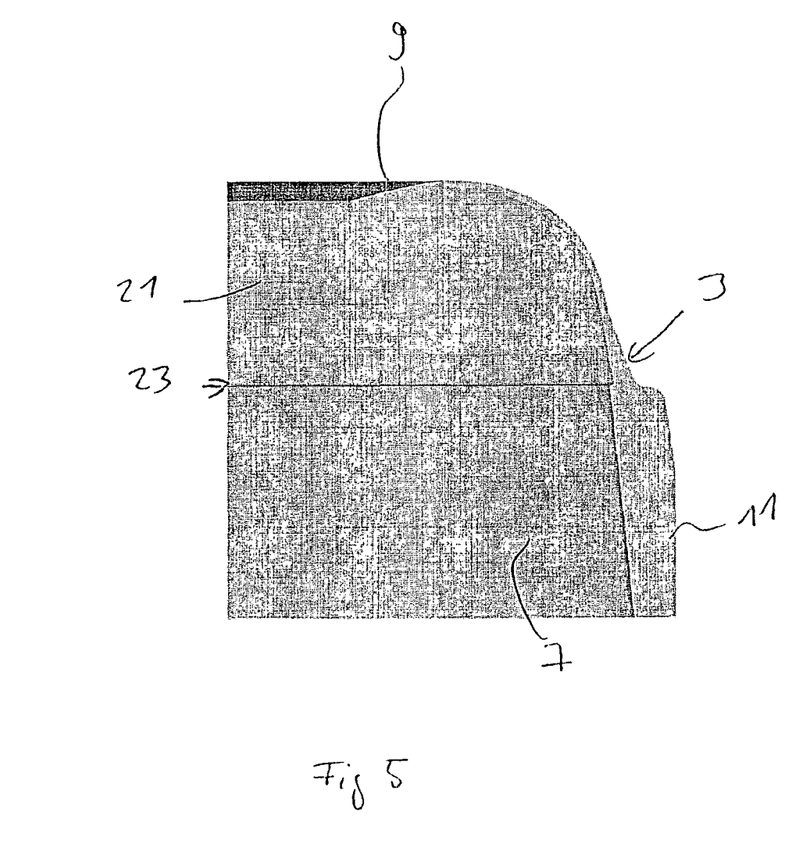
FIG. 5 is a schematic three dimensional cross-sectional view of a first component of a patient interface component according to an embodiment of the present invention.
Figure 6:
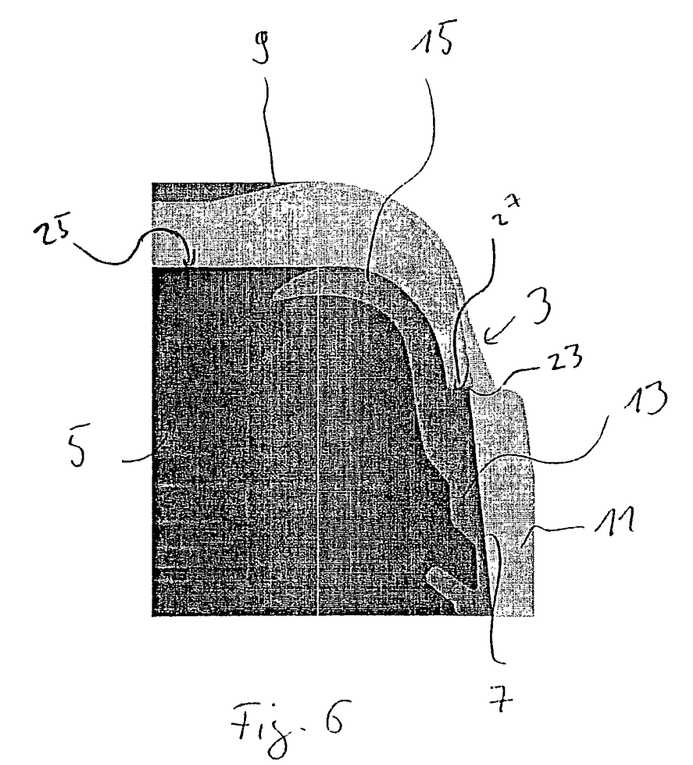
FIG. 6 is a schematic three dimensional cross-sectional view of a first and second component of a patient interface component according to the embodiment of the present invention shown in FIG. 5.

FIG. 5 shows a schematic three-dimensional perspective view on a first component 3 of a patient interface 1 having a thin membrane or sealing lip portion 9 and a connection portion 11 with an increased thickness vis-à-vis the sealing lip portion 9. Connection portion 11 provides a merging or contact surface 7 for contacting or merging with a corresponding surface of a second portion 5 (not shown in FIG. 5).

As previously discussed said first portion 3 is injection molded in a first step whereas in a second step the second portion 5 is co-molded to said first portion 3 and particularly to the merging surface or contact surface 7 of the first portion 3. Preferably, the tool for producing the patient interface or patient interface component comprises a first mold part (not shown) and a second mold part (not shown) which are adapted to define a first mold cavity therebetween for molding a first portion 3 of said patient interface component 1. Preferably, the first mold part comprises an inner surface corresponding to the outer surface of the first portion 3 wherein the first mold part furthermore preferably comprises a third cavity forming part of or an extension of said first cavity and providing inner and outer surfaces corresponding to the inner and outer surfaces of the sealing lip or thin membrane 9. According to said embodiment the first mold part is a construction extending (by providing said third cavity) around the outside of the first mold part 3 and through the opening of a patient interface component 1 established in the first mold part 3 (and second mold part 5) indicated in FIG. 1 as 19 to the inside of a first portion 3 for providing a surface corresponding to the inner surface 21 of thin membrane or sealing lip portion 9 thereby extending to a separation line 23 at a transition portion between membrane 9 and connecting portion 11. Such transition portion 23 is preferably a step provided in the inner surface of the first portion 3 where the inner surface of the sealing lip or membrane 9 is recessed vis-à-vis merging or connecting surface 7.

Said second mold part preferably tightly abuts to the first mold part in the region of transition line 23 and provides an outside surface corresponding to the inside surface of first portion 3 at connection or merging surface 7. The term inside is used to indicate a direction towards axis A in FIG. 1 whereas outside is used to indicate a direction away from said axis A.

After the first material has been injected into the first cavity provided between the second mold part and the first mold part and thereby also into the third cavity provided in the first mold part the second mold part is withdrawn and a third mold part (not shown) is inserted to define a second cavity. Said second cavity is suitable for injection molding the second portion 5 of the patient interface 1. Preferably, the inner surface of the second portion 5 is provided by an outer surface of said third mold part wherein an outer surface of the second cavity for injection molding the second portion 5 is provided by an inner surface of a portion of the first mold part and by the merging surface or connection surface 7 of the—already injection molded—first portion 3. In particular, the outer surface of the cushion portion 15 is defined by an inner surface of said portion of the first mold part the outside portion of which defines the inner surface 21 of the membrane or sealing lip 9. Preferably, the entire inner surface of the second portion 5 is defined by the outside of the third mold part.

Preferably, the first mold part defines a first mold half whereas the second mold part and third mold part, respectively, define a second mold half. Said first mold half is preferably located on or constitutes a turnable which is, after the second mold part has defined a first cavity together with a first mold part and after the first portion 3 has been injection molded simply extracted, turned and arranged in relation to the third mold to define, together with the already injected first portion 3 and/or the first mold part a third cavity for injection molding the second portion 5. Preferably, the tool is a brass tool.

The tool according to the present invention and thus the patient interface component produced therewith is preferably adapted so that a transition line 23 defining the mating ends of the connection or merging surface portion 3 and second portion 5, respectively, lies in a plane 27. Said plane 27 is preferably defined by a surface of the first mold part wherein the outer surface 25 of the cushion portion 15 and the inner surface 21 of the membrane or sealing lip 9 are stepped back from said transition line 23 so that both first portion 3 and second portion 5 comprise a step or shoulder at the end of the merging or connection surface 7, i.e., at transition line 23, which constitutes a corner line of each of said shoulders. Preferably, both shoulders define surface 27.

Figure 7A:
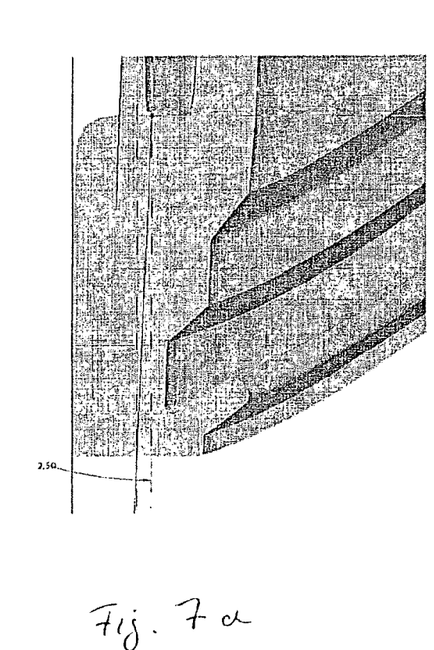
FIG. 7a shows a schematic three dimensional cross-sectional view of the transition zone between a first and a second component of the patient interface.
Figure 7B:
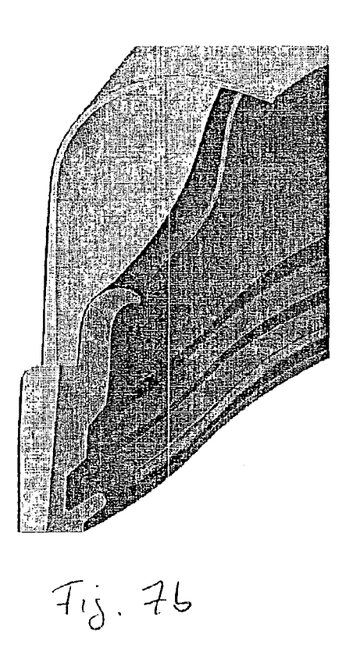
FIG. 7b shows a schematic three dimensional cross-sectional view of a first and a second component of the patient interface component.
Figure 7C:
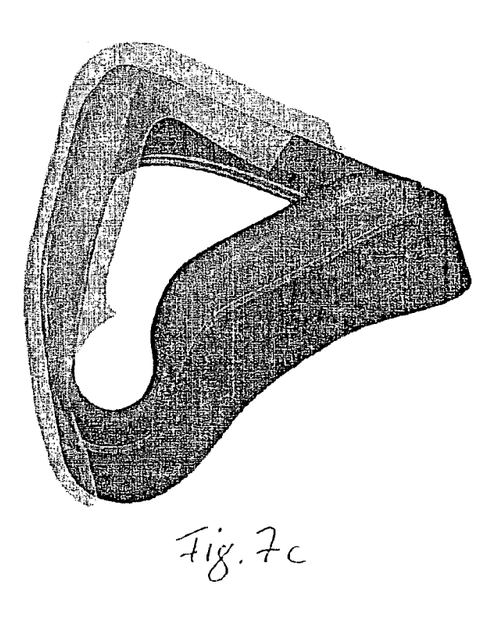
FIG. 7c shows schematic three dimensional, partly cross-sectional view on the patient interface component.
Figure 8:
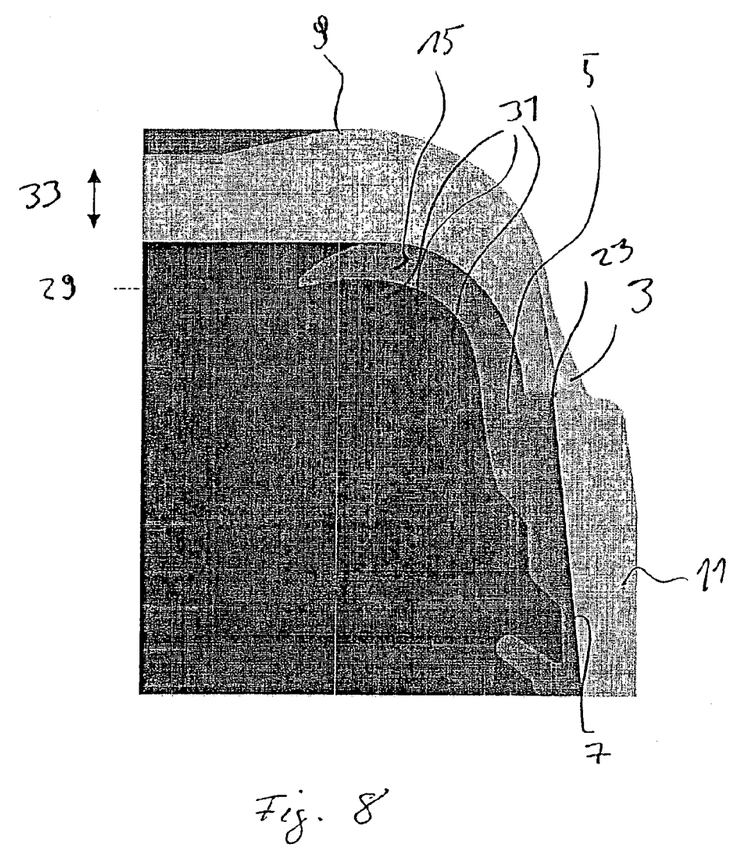
FIG. 8 is a schematic three dimensional cross-sectional view of a first and second component of a patient interface component according to an embodiment of the present invention.

As is apparent from, e.g., the broken lines shown in FIG. 8, the geometry of said first portion 3 and/or second portion 3 may be varied or adapted along the extension of the patient interface component 1 (see, e.g., FIG. 7B or FIG. 7C). Alternatively, the geometry of the respective portions or component may easily be adapted by simply changing the first mold part, the second mold part and/or the third mold part. Such adaptation provides an easy possibility to selectively adapt specific geometries of the patient interface component by merely replacing or adapting a part of the production tool.

FIG. 7 shows different schematic three-dimensional cross-sectional, partially cut views of a patient interface component according to the present invention which clarifies a preferred overall construction. According to said construction the sealing lip or membrane 9 extends over the cushion portion 15 thereby providing a contact zone for contacting the face of a wearer. As can be seen in FIG. 7A, a merging surface or contacting surface 7 is inclined by an angle $\alpha$ as already discussed above. Preferably, said angle $\alpha$ is defined as being inclined relative to the extraction or injection direction of the second mold part from the first mold part after the first portion 3 has been injection molded. In this manner, the longitudinal axis A extends in the demolding direction.

According to an alternative preferred embodiment, the second portion 5 is injection molded first and then the first portion 3 is injection molded. According to said alternative method, the respective method steps etc. as discussed above are correspondingly exchanged, as will be apparent for the person skilled in the art. Also, the mold parts will be adapted accordingly.

Preferred materials used for injection molding the first and/or second portion and/or other components of the patient interface or patient interface component elastomeric materials, silicone materials such as liquid silicone rubber or silicone foam etc.

In FIG. 8, 29 indicates a parting line between the first mold part and the second mold part as well as between the first mold part and the third mold part, wherein said parting line 29 simultaneously provides the circumference of opening 19 at the second portion 5. Arrows 31 indicate the variable change in thickness of, e.g., cushion portion 15 wherein arrow 33 indicates a change in distance between the sealing lip or membrane 9 and the cushion portion 15 based on the respective portion of the first mold part.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from sleep disordered breathing such as OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

The invention claimed is:

1. Component of a patient interface which seals with a patient face to deliver breathable gas under pressure to the patient's airway, comprising:
    a first portion having a first shore hardness; and
    a second portion having a second shore hardness different from the first shore hardness,
    wherein each of the first and second portions includes a connection portion co-molded to one another such that the first portion and the entire connection portion of the first portion are disposed radially outwardly of the second portion and the entire connection portion of the second portion, the first portion and the connection portion of the first portion forming an outer periphery of the component and the second portion and the connection portion of the second portion forming an inner periphery of the component,
    wherein at least the connection portion of the first portion is configured to provide a connection to an additional component of the patient interface, and
    wherein a contact area between the first and second portions is inclined, in a cross-sectional view, with respect to a longitudinal axis extending in a demolding direction.

2. Component according to claim 1, wherein the first and second portions are integrally formed.

3. Component according to claim 1, wherein the contact area is inclined by an angle lying in a range between about 0.5° and 20°.

4. Component according to claim 1, wherein the first portion comprises a thin membrane having a thickness of about 0.1 to 1 mm.

5. Component according to claim 1, wherein the component forms a cushion and wherein the second portion forms an under-cushion, which is thicker than the first portion and/or a membrane of the first portion.

6. Component according to claim 1, wherein part of the first portion is not in direct contact with the second portion and at least partially covers the first portion.

7. Component according to claim 1, wherein the first shore hardness is higher/harder than the second shore hardness.

8. Component according to claim 1, wherein the second shore hardness lies in a range between 1 and 40 shore A according to DIN 53505.

9. Component according to claim 1, wherein the first shore hardness lies in a range between 10 and 100 shore A according to DIN 53505.

10. Component according to claim 1, wherein the first and/or second portion comprises a polymer.

11. Component according to claim 1, wherein the contact area between the first and second portions is a substantially plane surface and/or a surface having a substantially plane cross-section.

12. Component according claim 1, wherein the component constitutes a face mask cushion, a forehead pad, and/or a component of a headband for securing a device at a wearer's head.

13. Method of producing a component according to claim 1, comprising the following steps:
    a) providing a molding tool having a first mold part and a second mold part which define a first mold cavity there between;
    b) injecting a first material having a first shore hardness into the first molding tool in order to provide a first portion of the component;
    c) removing the second mold part;
    d) providing a third mold part defining a second mold cavity between the first mold part and/or the first portion and the third mold part; and
    e) injecting a second material having a second shore hardness into the second mold cavity in order to provide a second portion integral with the first portion, wherein the second shore hardness is different from the first shore hardness.

14. Method according to claim 13, wherein the first shore hardness is larger than the second shore hardness.

15. Method according to claim 13, wherein the second shore hardness lies in a range between 1 and 40 shore A according to DIN 53505.

16. Method according to claim 13, wherein the first shore hardness lies in a range between 10 and 100 shore A according to DIN 53505.

17. Method according to claim 13, wherein the second material is co-molded to the first portion.

18. Method according to claim 13, wherein the first mold part is defined by a first mold half and wherein the second mold part and the third mold part are defined by separate second mold halves, respectively, wherein said first mold part is moved from the second mold part to the third mold part by a turntable.

19. Method according to claim 13, wherein the first mold part comprises a third cavity for molding a part of the first portion while injecting the first material.

20. Method according to claim 13, wherein the first and/or second material comprises a colour.

21. Tool for manufacturing a component according to claim 1, comprising a first mold part.

22. Tool according to claim 21, further comprising a second mold part, wherein the first mold part and the second mold part define a first mold cavity there between, and comprising a third mold part which defines a second mold cavity between the first mold part and the third mold part.

23. Tool according to claim 22, wherein the first mold cavity is adapted to be filled with a first material in a first injection shot and wherein the second mold cavity is adapted to contain the first material and to be filled with a second material in a second injection shot.

24. Tool according to claim 22, wherein the first mold half is defined by a first mold part and wherein the second mold part and the third mold part are defined by separate second mold halves, respectively, wherein said first mold half is adapted to move from the second mold part to the third mold part and vice versa by turning the first mold half on a turntable.

25. Tool according to claim 22, wherein the first mold part comprises a third cavity for molding a part of the first portion while injecting the first material.

26. A breathing mask comprising:
    a component according to claim 1.

27. Component according to claim 3, wherein the angle is in a range between about 1° and 12°.

28. Component according to claim 27, wherein the angle is in a range between about 2° and 6°.

29. Component according to claim 28, wherein the angle is about 2.5°.

30. Component according to claim 3, wherein the angle is at least 2°.

31. Component according to claim 4, wherein the thickness is about 0.35 mm.

32. Component according to claim 8, wherein the second shore hardness lies in a range between 3 and 25 shore A according to DIN 53505.

33. Component according to claim 32, wherein the second shore hardness lies in a range between 5 and 10 shore A according to DIN 53505.

34. Component according to claim 9, wherein the first shore hardness lies in a range between 20 and 60 shore A according to DIN 53505.

35. Component according to claim 34, wherein the first shore hardness lies in a range between 40 and 50 shore A according to DIN 53505.

36. Component according to claim 10, wherein the polymer is one of polysiloxane, silicone, silicone foam, liquid silicone rubber, and/or thermoplastic elastomer.

37. Method according to claim 15, wherein the second shore hardness lies in a range between 3 and 25 shore A according to DIN 53505.

38. Method according to claim 37, wherein the second shore hardness lies in a range between 5 and 10 shore A according to DIN 53505.

39. Method according to claim 16, wherein the first shore hardness lies in a range between 20 and 60 shore A according to DIN 53505.

40. Method according to claim 39, wherein the first shore hardness lies in a range between 40 and 50 shore A according to DIN 53505.

41. Component according to claim 1, wherein the contact area between the first and second portions is substantially linear.

* * * * *

UNITED STATES PATENT AND TRADEMARK OFFICE
CERTIFICATE OF CORRECTION

PATENT NO. : 9,010,331 B2
APPLICATION NO. : 12/735728
DATED : April 21, 2015
INVENTOR(S) : Lang et al.

Page 1 of 1

It is certified that error appears in the above-identified patent and that said Letters Patent is hereby corrected as shown below:

In the claims:

In claim 1, at column 13, line 10, "which seals with a patient face to deliver breathable gas under pressure to the patient's airway" should be corrected to ---which seals with a patient's face to deliver breathable gas under pressure to the patient's airways---

Signed and Sealed this
Fifteenth Day of December, 2015

Michelle K. Lee
*Director of the United States Patent and Trademark Office*